United States Patent [19]

Pappas

[11] Patent Number: 5,735,904
[45] Date of Patent: Apr. 7, 1998

[54] SPACER FOR ESTABLISHNG PROSTHETIC GAP AND LIGAMENTOUS TENSION

[76] Inventor: Michael J. Pappas, 61 Gould Pl., Caldwell, N.J. 07006

[21] Appl. No.: 666,085

[22] Filed: Jul. 1, 1996

[51] Int. Cl.[6] ........................................ A61F 2/38
[52] U.S. Cl. .............................. 623/20; 606/86; 606/88; 606/90; 606/102
[58] Field of Search ............... 623/20, 22, 23, 623/18; 606/86, 99, 102, 88–90, 100

[56] References Cited

U.S. PATENT DOCUMENTS

| 4,211,228 | 7/1980 | Cloutier | 606/102 |
|---|---|---|---|
| 4,566,466 | 1/1986 | Ripple et al. | 606/102 |
| 5,207,711 | 5/1993 | Caspari et al. | 623/20 |
| 5,213,112 | 5/1993 | Niwa et al. | 606/90 |
| 5,234,433 | 8/1993 | Bert et al. | 606/102 |
| 5,445,642 | 8/1995 | McNulty et al. | 606/102 |
| 5,464,406 | 11/1995 | Ritter et al. | 606/86 |
| 5,520,695 | 5/1996 | Luckman | 606/88 |
| 5,540,696 | 7/1996 | Booth, Jr. et al. | 606/102 |
| 5,597,379 | 1/1997 | Haines et al. | 606/90 |
| 5,649,928 | 7/1997 | Grundei | 606/86 |

FOREIGN PATENT DOCUMENTS 9014806  12/1990  WIPO ........................... 623/20

Primary Examiner—Michael J. Milano
Assistant Examiner—Tram Anh T. Nguyen
Attorney, Agent, or Firm—Anthony J. Casella; Gerald E. Hespos; Ludomir A. Budzyn

[57] ABSTRACT

A system of templates is provided for use during implantation of a prosthetic joint. The templates are of different surface areas and different thicknesses. The templates are first used to enable selection of a prosthetic component corresponding to the shape of a resected bone into which the prosthetic component will be implanted. The templates are then used to establish an appropriate prosthetic gap for the selected prosthetic component. The prosthetic gap will vary in accordance with the selected prosthetic component.

15 Claims, 13 Drawing Sheets

SPACER FOR ESTABLISHING PROSTHETIC GAP AND LIGAMENTOUS TENSION

This application claims the benefit of U.S. Provisional Application No. 60/000,790, filed Jul. 5, 1995, now abandoned.

BACKGROUND OF THE INVENTION

1. Field of the Invention

The subject invention relates to a system of spacers for use during the implantation of prosthetic joints to achieve proper tension in retained ligaments of the joint.

2. Description of the Prior Art

A prosthetic joint includes first and second prosthetic components that are mounted respectively to first and second bones of a joint. The first and second bones of the joint must be resected to define surfaces that are properly configured, aligned and disposed to receive the prosthetic components.

Prosthetic joint replacement surgery is complicated by the fact that not all patients are the same size. Prosthetic components, therefore, must be dimensioned to substantially match the anatomy of the patient into which the prosthetic components are to be implanted.

Most manufacturers of prosthetic joints produce a system of dimensionally different, but structurally and functionally similar prosthetic components. Templates are used to gauge the size of a resected bone. Each template has a correspondingly configured and dimensioned prosthetic component. The surgeon selects the template that most closely conforms to the resected bone and then selects the corresponding prosthetic component for implantation.

Surgical preparation of the joint also must ensure proper tension in retained ligaments. Tension can be gauged by placing a spacer that corresponds to the thickness of the implant between the bones. If the spacer is too tight, the bones may have to be resected further. If the spacer block is too loose, the surgeon may have to use a thicker component.

To simplify surgery and to make the inventory of tools more manageable, prior art systems of prosthetic joints have been manufactured to permit a common prosthetic gap for a broad range of differently dimensioned prosthetic components. In this context, prosthetic gap refers to the distance between the resected bone surfaces. The use of a common prosthetic gap permits the use of a single universal spacer for ensuring optimum tension in ligaments that are retained post-operatively.

Although the prior art prosthetic joint system and surgical procedure offer many advantages, there are certain potential disadvantages. For example, larger prosthetic components necessarily will be used with thinner bearings if the prosthetic gap is to be constant and if the same spacer is used for both large and small prosthetic components. This is undesirable in that the larger patient in which the larger prosthetic component is implanted will exert greater loads on the bearing. A thinner bearing will have a lower load bearing capacity and a potentially shorter functional life. Hence, the surgical convenience of a constant prosthetic gap and use of a single spacer block is obtained at the expense of a decreased load bearing capacity and a potentially shorter functional life for the prosthetic joint. Some prosthetic joint systems may permit the same bearing thickness to be used for a small range of differently dimensioned prosthetic components. This may be acceptable, but is not optimal. In particular, the common bearing thickness may not provide the greater load bearing capacity that may be required by a larger patient with a larger prosthetic component.

The prior art use of templates and spacers during the implantation of a prosthetic joint can best be illustrated in the context of a prior art knee prosthesis. In particular, a prior art knee prosthesis is illustrated in FIGS. 1 and 2, and is identified generally by the numeral 100. The prosthesis 100 is for implantation between a femur 102 and a tibia 104. The prosthesis 100 includes a femoral component 106 having a superior portion 108 for mounting to the distal end of a femur 102 and an inferior articular bearing surface 110. The prior art prosthesis 100 further includes a tibial component 112 having an inferior portion 114 for mounting to the proximal end of a tibia 104 and a superior bearing surface 116. A plastic bearing 118 is disposed between the femoral component 106 and the tibial component 112 of the prior art prosthesis 100. The bearing 118 has an inferior surface 120 in bearing relationship to the superior surface 116 of the tibial component 112 and a superior surface 122 in articular bearing engagement with the inferior articular bearing surface 110 of the femoral component 106. The prior art prosthesis 100 comes in a range of different sizes to match the size of the patient.

A prior art template used during implantation of the prior art prosthesis 100 is illustrated in FIGS. 3 and 4 and is identified by the numeral 124. The prior art template 124 is an elongate planar member having opposed ends 126 and 128 which are of slightly different plan view shapes and sizes. The template 124 is one of several templates available to a surgeon, with the respective template ends having different sizes and shapes, but uniform thicknesses. Each template end 126 and 128 is provided with indicia 130 and 132 respectively which identifies a particular size prior art tibial component 112. The surgeon selects the template end providing the best coverage of the resected tibia 104 without overhang and then selects the corresponding tibial component. As shown in FIG. 4, the physician may further use the template 124 in combination with a reciprocating saw to make vertical cuts for accommodating retained ligaments.

An example of one of the many prior art surgical techniques for implantation of a knee prosthetic joint employs a prior art femoral resection guide 134 as shown in FIGS. 5-7 and a femoral resection guide spacer 136 as shown in FIGS. 6 and 7. These components are described in detail in U.S. Patent No. 4,738,254, entitled "POSITIONER FOR SURGICAL INSTRUMENTS" which issued on Apr. 19, 1988 to M. J. Pappas and F. F. Buechel, the disclosure of which is incorporated herein by reference. Briefly, the femoral resection guide 134 is used by the surgeon to guide the saw blade during resection of the femur 102. The femoral resection guide spacer 136 is used to position the femoral resection guide 136 relative to the resected tibia 104 to ensure that the femoral resection is carried out to reproduce the flexion gap and to balance medial and lateral ligamentous tension. If the fit of the femoral resection guide spacer 136 is too tight, the superior surface of the resected tibia 112 is further resected to achieve a proper fit of the femoral resection guide spacer 136. If the femoral resection guide spacer 136 is too loose, an appropriately thick adaptor 138a–d, as shown in FIG. 8, is installed onto the inferior surface of the spacer 136. The thickness adapters 138a–d necessarily must have a plano-configuration conforming in size and shape to the smallest resected tibia. When these small thickness adapters 138a–d are used on a large patient, they will contact only the central portion of the resected tibia which is comprised of soft compressible bone tissue. The small thickness adapters 138a–d thus can compress or otherwise damage the soft bone tissue, particularly when ligamentous tension is being checked. Bone damage is particularly problematic because many patients are having this surgery to repair an existing condition of weak or diseased bone. The inventor herein recognized that the potential for bone damage can be overcome by providing a set of thickness adapters for each size prior art prosthetic component. However, this would substantially multiply the number of tools required for surgery and would complicate the surgical procedure.

The prior art surgical technique proceeds as shown in FIGS. 9-11 by using a resection checking spacer 140 in combination with any thickness adaptor 138a-d that may have been required for use with the femoral resection guide spacer 136 to re-approximate the flexion prosthetic gap. Further adjustment of the tibial resection may be required. In making any resection adjustments, the surgeon must ensure that the extension gap equals the flexion gap. The resection checking spacer 140 must have a plano-configuration sized and shaped to fit the smallest resected tibia. However, as with the thickness adapters 138a-d described above, when the common resection checking spacer 140 is used on a larger patient, it will contact only the soft central part of the resected bone. This soft central bone tissue may be compressed when ligamentous tension is checked. Thus the prior art resection checking spacer 140 may damage the resected bone and reduce the contact area between the bone and prosthetic component.

Returning to FIG. 1, the prosthetic components 106 and 112 and the bearing 118 are selected to achieve proper fit on the bones 102 and 104 and to achieve a uniform prosthetic gap "A" for which the common or universal spacer block is dimensioned. It will be appreciated that as the femoral component 106 of the prosthesis 100 increases in size, the distal and posterior portions 106d and 106p are necessarily thicker. Thus, to maintain the constant prosthetic gap "A" throughout the system, the system must include a plurality of different bearings 118 of different respective thicknesses. Hence, thinner bearings 118 will be used with the larger prosthetic components. As noted above, however, thin bearings have a lower load bearing capacity and a potentially shorter life.

Accordingly, it is an object of the subject invention to provide a prosthetic system that does not require a reduction in bearing thickness with an increase in the prosthetic component size.

It is another object of the subject invention to provide a prosthetic system that enables an increase in the prosthetic gap for larger prosthetic components without complicating the bone resectioning process.

It is a further object of the subject invention to provide a prosthetic system for achieving an optimally dimensioned prosthetic bearing and an optimally dimensioned prosthetic gap, while using a system of tools employing only a single resection guide spacer and a single resection checking spacer for implanting the prosthetic joint in a manner that ensures optimum tension in ligaments that are retained post-operatively.

A further object of the subject invention is to provide a system of tools that can be used during joint replacement surgery with damaging portions of the bones that are retained.

SUMMARY OF THE INVENTION

The subject invention is directed to a prosthetic system for implanting a prosthetic replacement joint. The prosthetic replacement joint comprises first and second prosthetic components for implantation respectively in or on first and second bones of the natural joint. The prosthetic joint further comprises a bearing disposed between the first and second prosthetic components. The first and second prosthetic components may be formed from a metallic material and the bearing may be formed from a non-metallic material.

The prosthetic system comprises a plurality of such prosthetic replacement joints including at least one joint in each of a plurality of different sizes. The differently dimensioned prosthetic joints are intended for implantation in patients having differently dimensioned and configured bone structures. Typically smaller prosthetic joints are to be implanted in smaller patients, while larger prosthetic joints are to be implanted in larger patients.

The subject invention further comprises a system of tools for implanting the prosthetic joints. The system of tools includes a single resection guide spacer suitable for use with each of a plurality of differently dimensioned prosthetic joints in the system and a single resection checking spacer which also is suitable for use with each of the plurality of differently dimensioned prosthetic joints. The two spacers are used respectively to guide and check the resection and to ensure optimum tension in ligaments that are retained post-operatively.

The system of tools further includes a plurality of templates corresponding to the plurality of different sizes of prosthetic joints in the system. The templates have different plan view sizes and shapes corresponding respectively to possible sizes and shapes for a resected bone to ensure that the resected bone will properly mate with a corresponding prosthetic component. Unlike prior art systems, the templates in the subject system are not of uniform thickness. Rather, template thickness increases with plan view area, such that large area templates also are thicker. Each template can be mounted to the resection guide spacer or to the resection checking spacer, and the combination of the template and the spacer provide a greater prosthetic gap for larger templates. Templates defining larger surface areas and corresponding to larger bones and larger prosthetic components achieve larger prosthetic gaps. Conversely, templates defining smaller cross-sectional areas and intended for smaller bones and smaller prosthetic components achieve smaller prosthetic gaps. The increase in prosthetic gaps with larger prosthetic components enables the desirable use of thicker bearings with larger prosthetic components.

The system of tools achieves another significant advantage. In particular, the templates mount to the spacers such that the template can be placed against the resected bone that the template was used to gauge. Thus the portion of the combined spacer/template that engages the resected bone very closely conforms to the shape of the resected bone. As a result, soft inner portions of the bone will not be damaged or crushed when ligamentous tension is checked as had occurred in the prior art.

The system is used by resecting the first and second bones of the joint using surgical guides that may be part of the system. The subject templates are used to select a prosthetic component that matches the size and shape of the resected bone. The template selected for a particular prosthetic joint of the system is then used with the common resection guide spacer and the common resection checking spacer to achieve the proper prosthetic gap and to enable selection of a bearing having a thickness appropriate for the size and shape of the resected bone. Each spacer may be adjusted in accordance with the ligamentous tension. The resection may proceed incrementally, if necessary until the prosthetic gap equals the combined thickness of the spacer and the selected template. As a result, a relatively larger prosthetic joint for a relatively larger patient will be used with the correspondingly large template and the spacer to ensure that a relatively large prosthetic gap is achieved between the resected bone surfaces of the joint. Conversely, using this same procedure, a smaller patient with a smaller prosthetic joint will use a smaller template and the spacer block to achieve a smaller prosthetic gap.

The system of the subject invention ensures that larger patients will not be handicapped by the implantation of a prosthetic joint with an undesirably thin bearing. Rather, larger patients will benefit from a prosthetic joint having a bearing of appropriate thickness for accommodating the loads imposed thereon by the larger patient. Thus, the bearing and the entire prosthetic joint are likely to achieve a longer functional life. Additionally, and significantly, the provision of different prosthetic gaps for differently dimensioned prosthetic components can be achieved without increasing the number or complexity of tools required for surgical implantation of the prosthetic joint. Furthermore, the system of the subject invention eliminates the requirement of the use of thickness adaptors.

DETAILED DESCRIPTION OF THE PREFERRED EMBODIMENT

Figure 1:
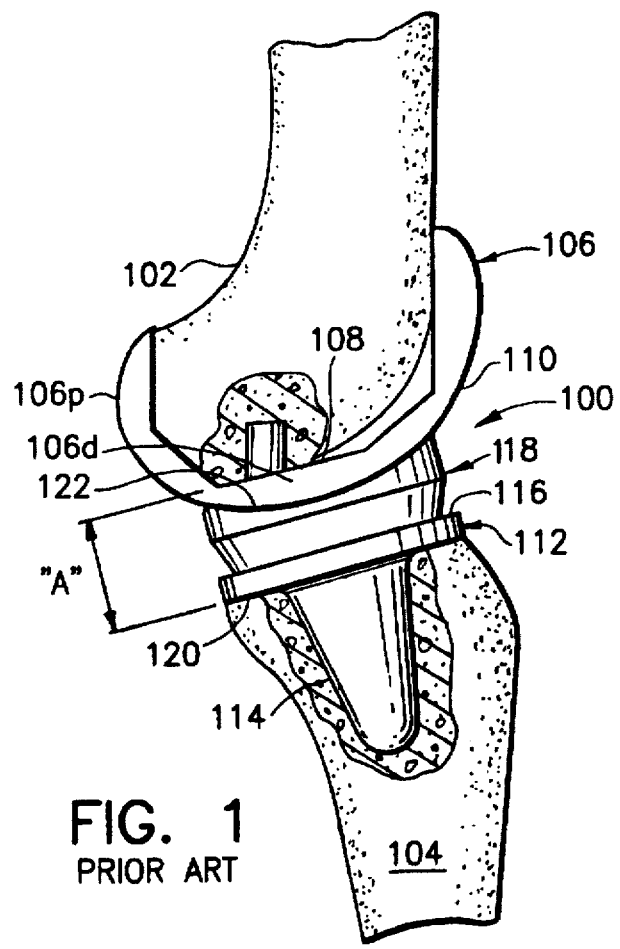
FIG. 1 is a side elevational view of a prior art prosthetic joint.
Figure 2:
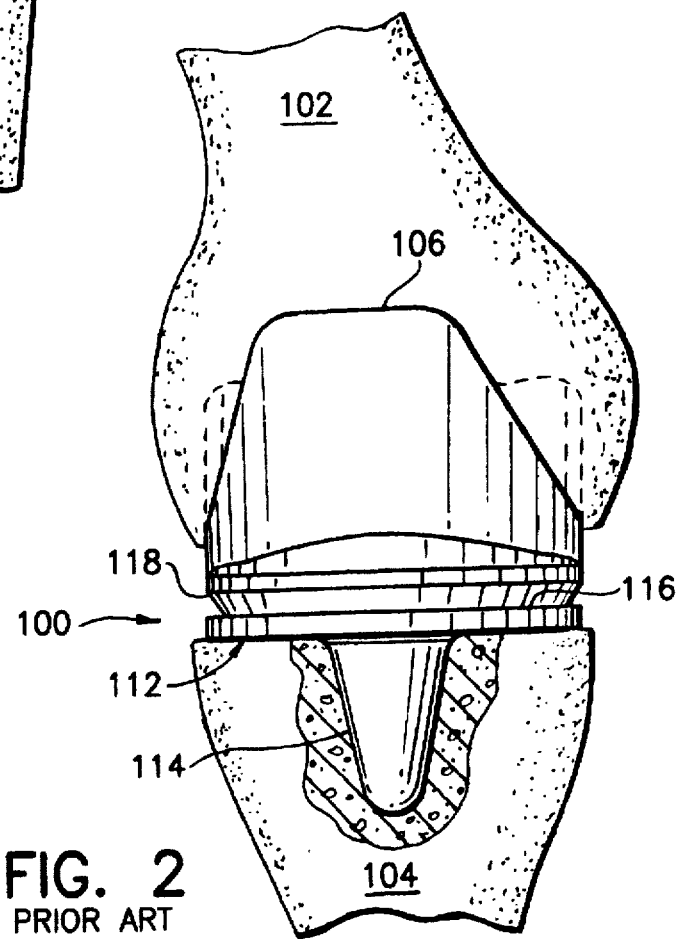
FIG. 2 is a front elevational view of the prior art joint shown in FIG. 2.
Figure 3:
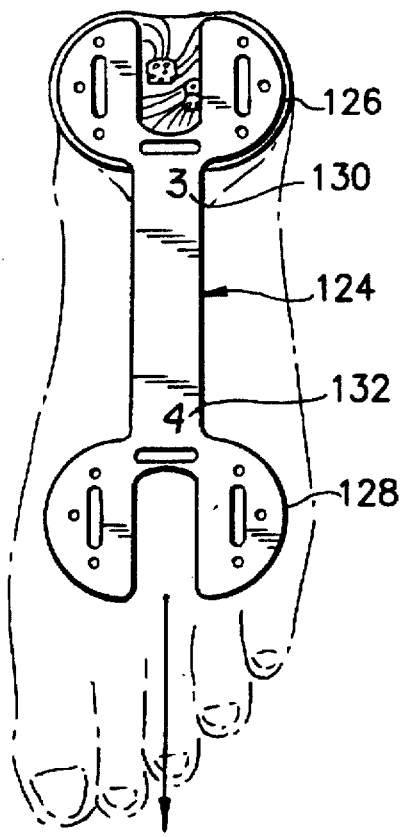
FIG. 3 is a top plan view of a prior art tibial template.
Figure 4:
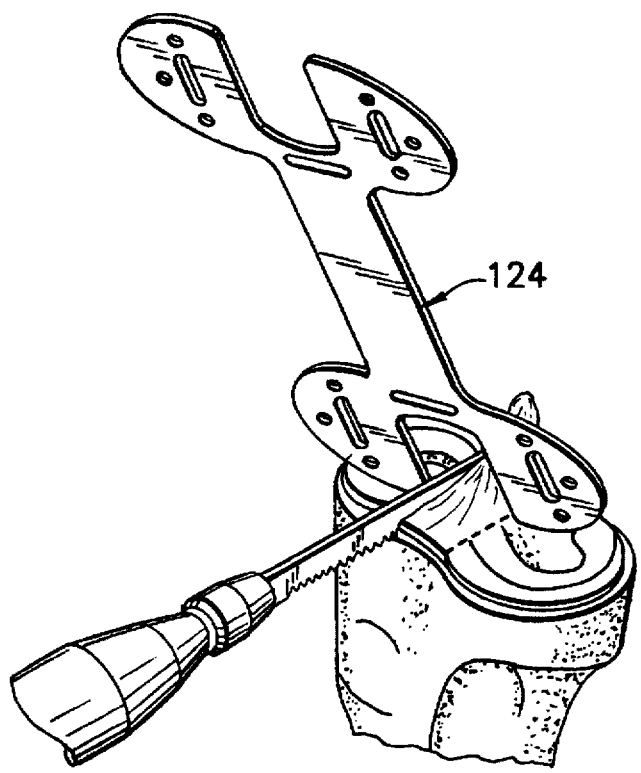
FIG. 4 is a prospective view of a prior art tibial template in use.
Figure 5:
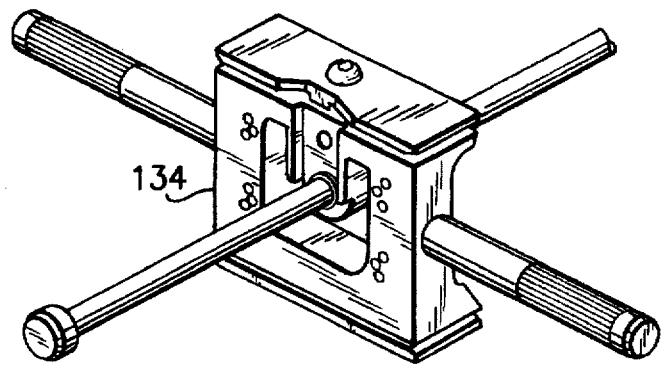
FIG. 5 is a perspective view of a prior art femoral resection guide.
Figure 6:
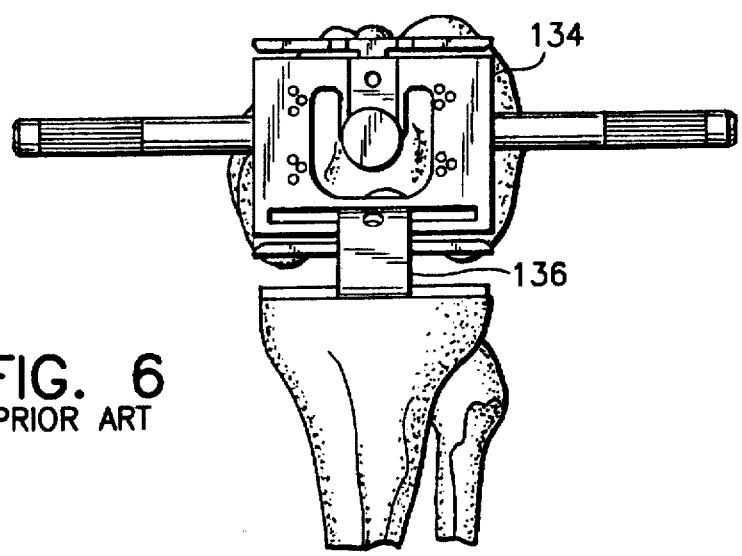
FIG. 6 is a front elevational view of the prior art femoral resection guide in use with a prior art femoral resection guide spacer.
Figure 7:
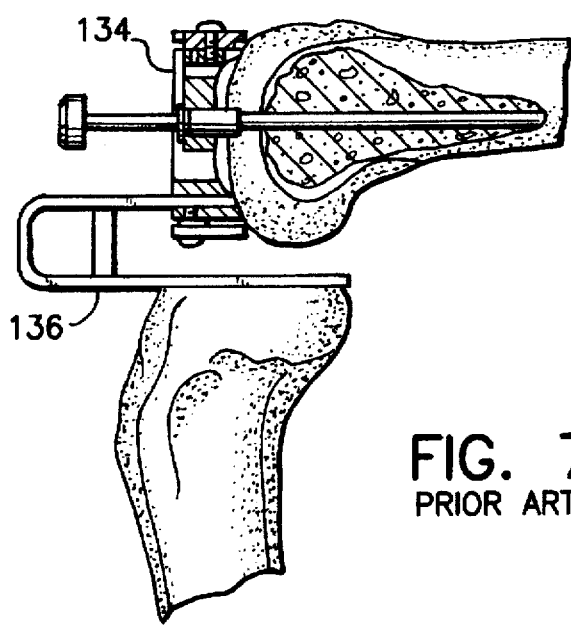
FIG. 7 is a side elevational view of a prior art femoral resection guide and spacer of FIG. 6.
Figure 9:
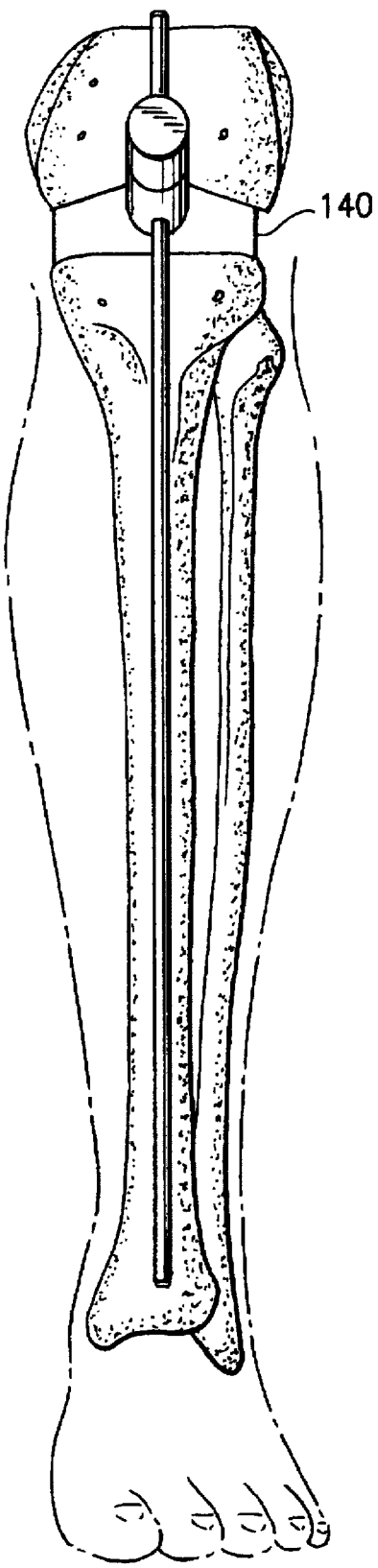
FIG. 9 is a front elevational view of a prior art spacer block in use.
Figure 8:
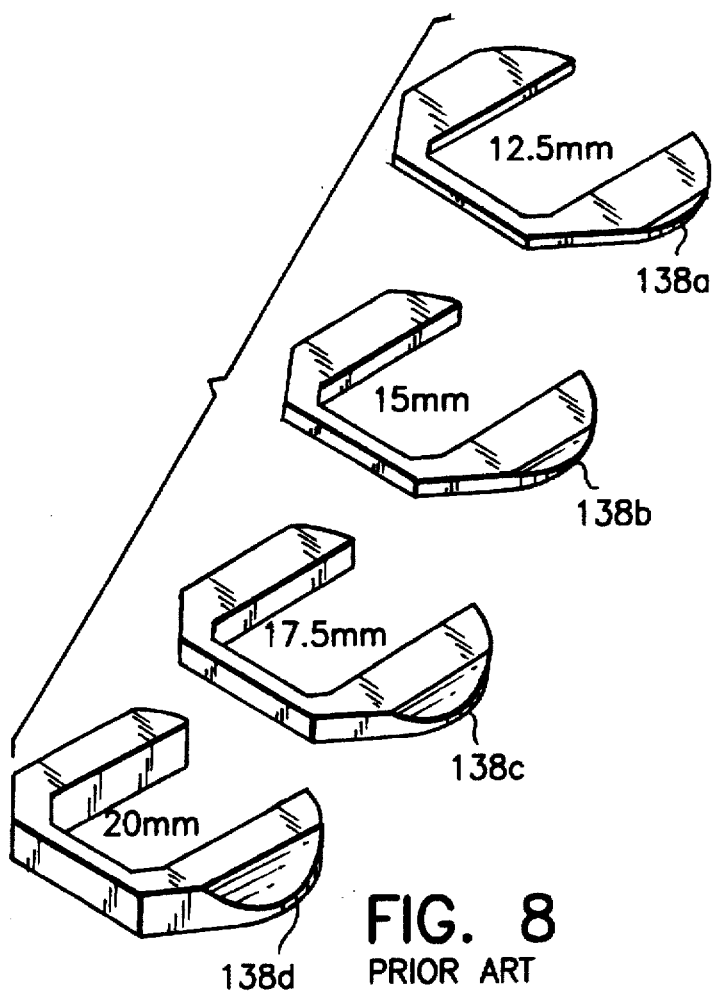
FIG. 8 is a perspective view of a set of thickness adaptors for use with the prior art resection guide and spacer.
Figure 10:
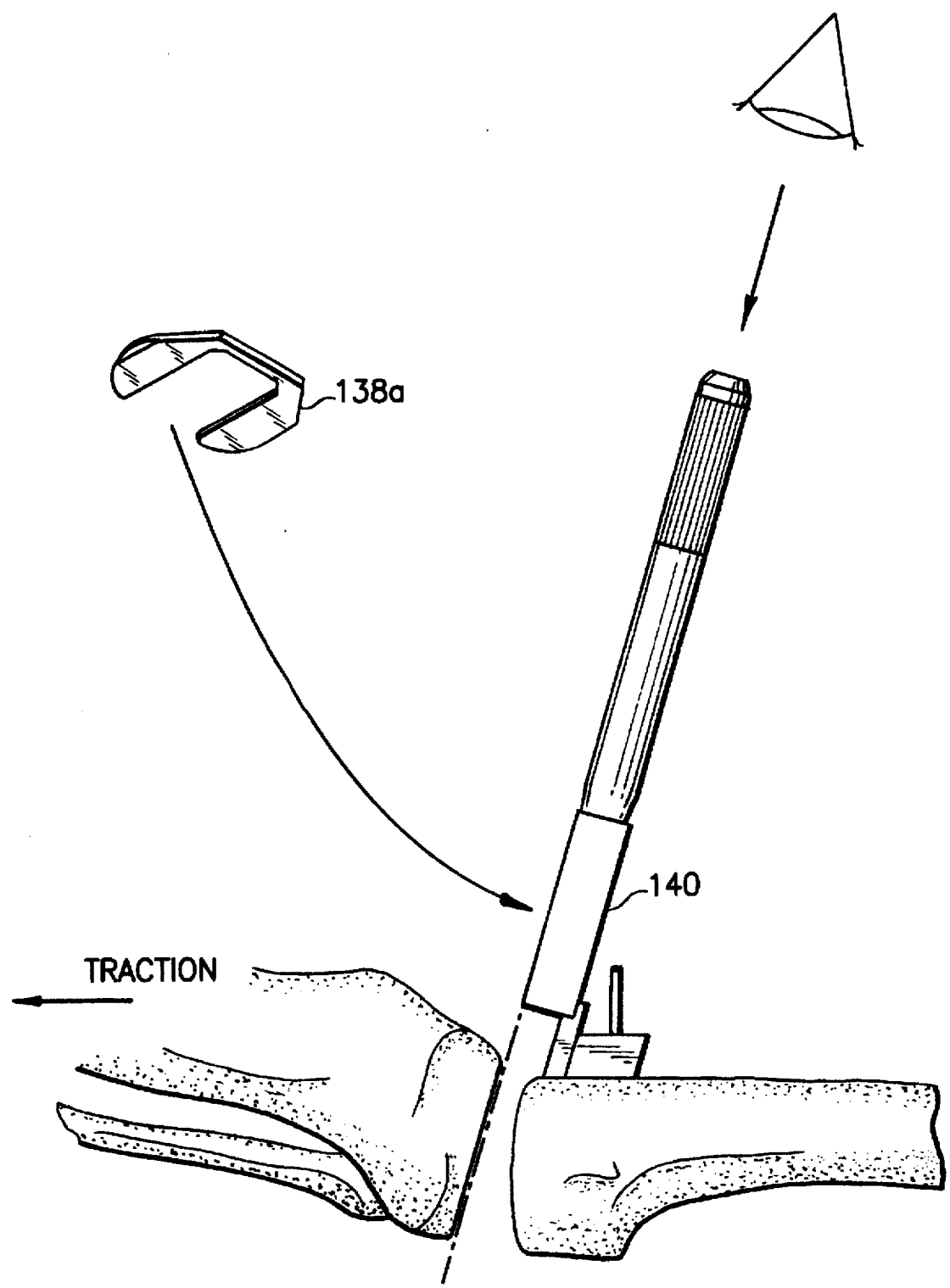
FIG. 10 is an exploded elevational view of a prior art spacer block used with the prior art thickness adaptor.
Figure 11:
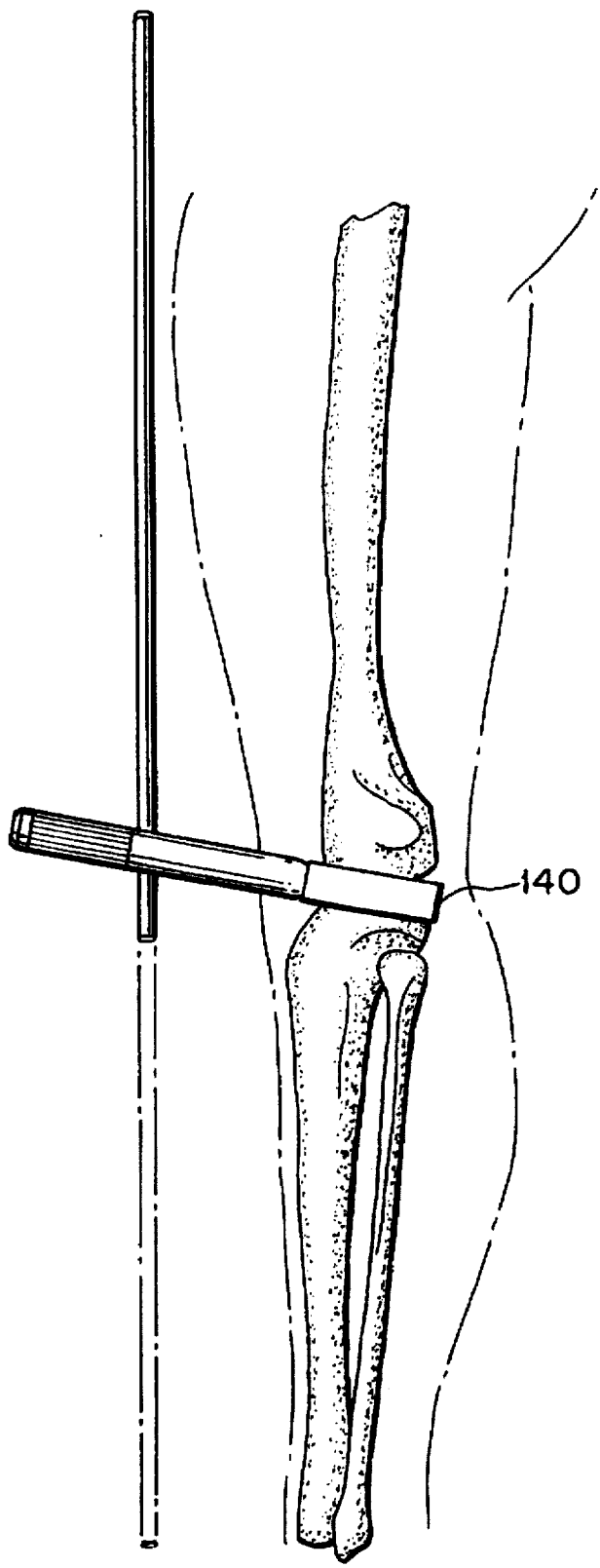
FIG. 11 is a side elevational view of the prior art spacer block.

The subject invention is directed to a prosthetic joint replacement system that may be particularly adapted for knee joint replacements. The prosthetic knee joint replacement system may include femoral components, tibial components and bearings all of which are similar to the corresponding components in the prior art system described above and illustrated in FIGS. 1 and 2. However, unlike the prior art systems, the prosthetic joint replacement system of the subject invention does not require a uniform prosthetic gap across a range of prosthetic component sizes, and hence enables a substantially thicker bearing for use with larger prosthetic components in the system. These advantages are achieved as described herein without complicating the surgical procedure and without increasing the number of tools required for performing the surgical procedure. Furthermore, the tools used to achieve and check the prosthetic gap and ligamentous tension have a plan view of shape or footprint conforming to the shape of the resected bone. Consequently the probability of compression damage of soft bone tissue during surgery is substantially reduced.

Figure 12:
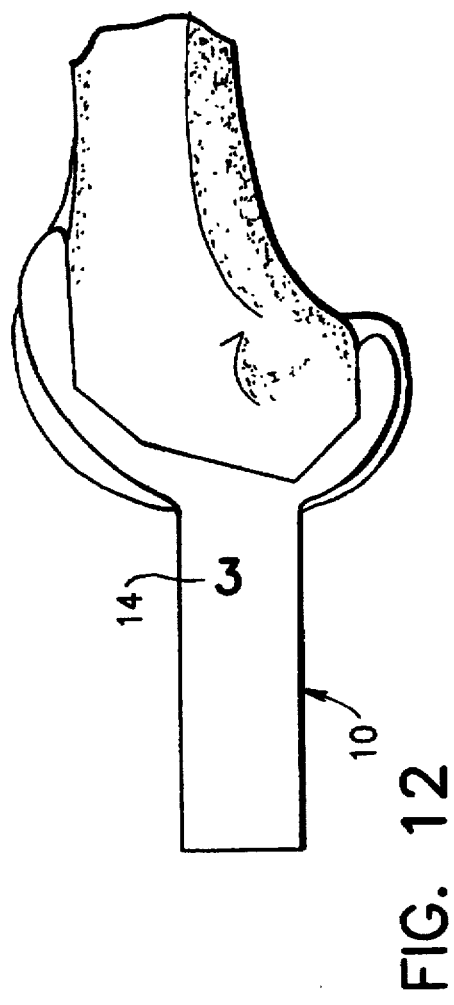
FIG. 12 is a side elevational view of a femoral template.

A femoral template 10 as shown in FIG. 12 and a tibial template 12 as shown in FIGS. 13–16 are employed with the spacing system of the subject invention. The femoral template 10 and tibial template 12 are used for sizing the bone to select the optimum size prosthetic components. In particular, the femur is resected such that all femoral osteophytes are removed whereby the normal femoral shape can be visualized. The surgeon then selects a femoral template 10 that best approximates the bony profile of the lateral femoral condyle independent of any articular cartilage. Each of the femoral templates 10 is provided with indicia 14 for identifying a particular size prosthesis.

Figure 13:
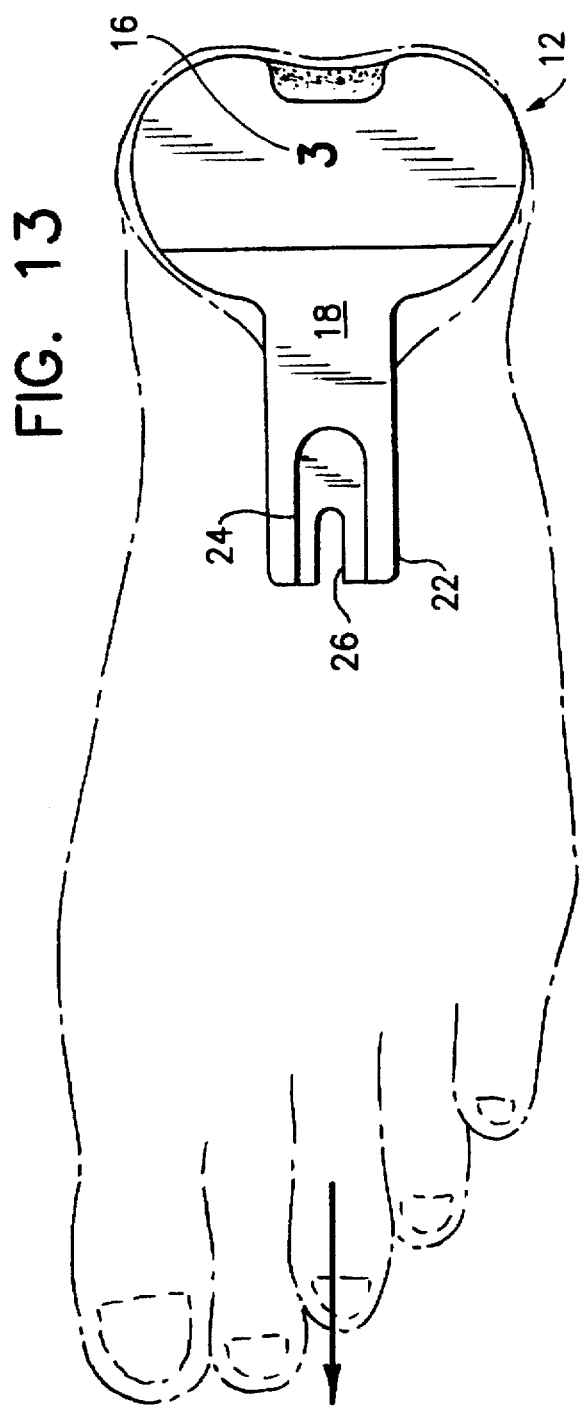
FIG. 13 is a top plan view of a tibial template.

The surgeon then checks the tibial component fit by selecting the tibial template 12 which is the same size as the selected femoral template 10 that had provided the best femoral fit. In this regard, as shown in FIG. 13, the tibial component 12 is provided with indicia 16 corresponding to the indicia 14 on the femoral component 10 and further corresponding to the various prosthetic components that can be used. The selected tibial template 12 is placed on the resected tibial plateau as shown in FIG. 13. The tibial template 12 should fit without substantial overhang. If excessive overhang is present, the next smaller size components for both the femur and tibia should be used.

Figure 14:
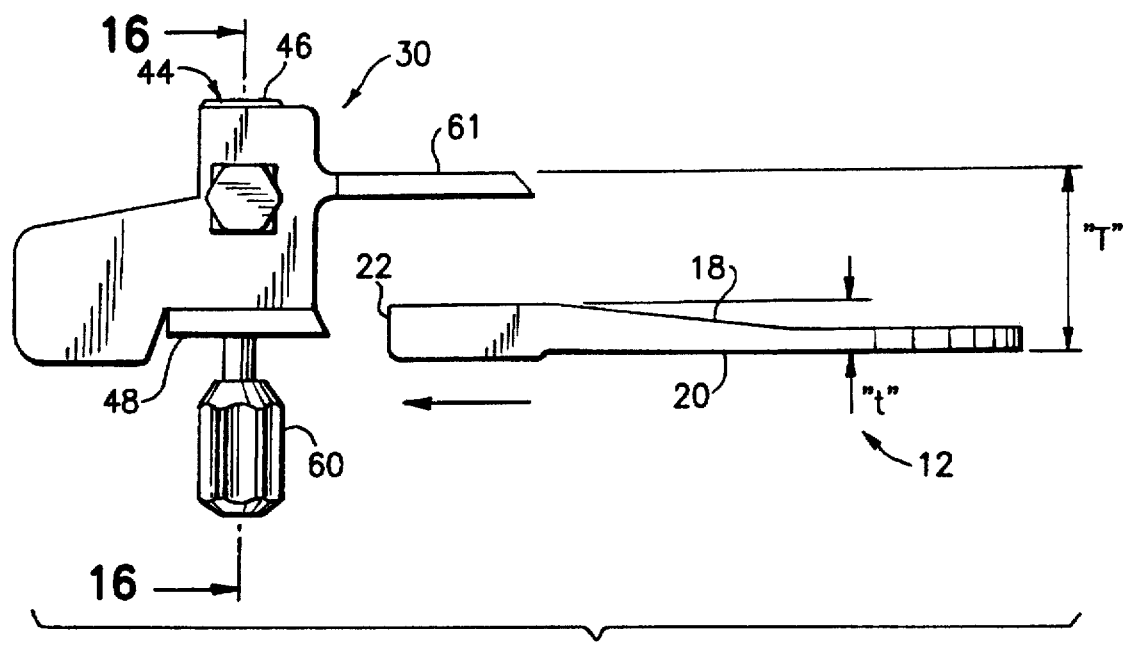
FIG. 14 is an exploded side elevational view of a tibial template and a femoral resection guide spacer.

The tibial template 12 has opposed superior and inferior surfaces 18 and 20, as shown most clearly in FIG. 14.

Additionally, the tibial template 12 has a handle 22 extending from portions of the tibial template 12 used to gauge the size of the resected tibial plateau. The handle 22 defines a thickness "t" as shown most clearly in FIG. 14. The thickness "t" varies from one tibial template 12 to another such that larger tibial templates 12 have a handle of greater thickness "t". The variation in thickness of the handle 22 is achieved by the taper in the superior surface 18 thereof.

Figure 16:
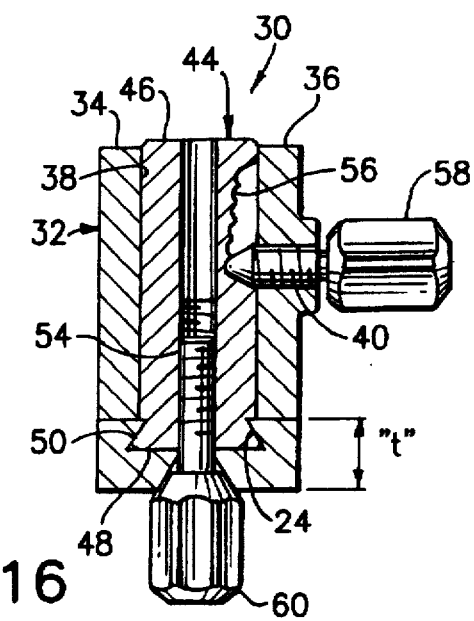
FIG. 16 is a cross-sectional view taken along line 16—16 in FIG. 14.

The handle 22 of the tibial template 12 is characterized by a dovetailed slot 24 extending into the superior surface 18, as shown in FIGS. 13 and 16. The dovetail slot 24 on all tibial templates 12 in the system is of substantially the same configuration. However, the distance between the base of the dovetailed slot 24 and the inferior surface 20 of the tibial template 12 will vary depending upon the thickness "t" of the handle 22 which, in turn, will vary in accordance with the size of the gauging portion of the tibial template 12. The handle 22 of the tibial template 12 is further characterized by a through slot 26 extending entirely therethrough from the superior surface 18 to the inferior surface 20 and communicating with the dovetailed slot 24.

Figure 15:
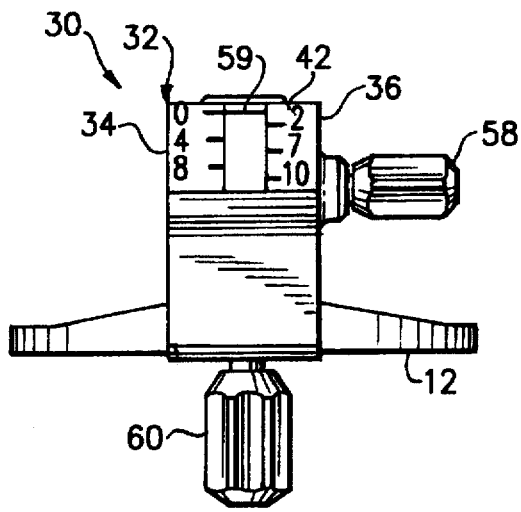
FIG. 15 is a front elevational view of the femoral resection guide spacer assembled to the tibial template.

The tibial template 12 is used with a femoral section guide spacer 30 as shown in FIGS. 14–16. The femoral resection guide spacer 30 includes a housing 32 having a pair of side walls 34 and 36 and a slot 38 therebetween, as shown most clearly in FIG. 16. The side wall 36 includes a threaded aperture 40 extending therethrough and into the slot 38. The side walls 34 and 36 also include indicia 42 as shown in FIG. 15. The function of the indicia 42 will be described further below.

The femoral resection guide spacer 30 further includes a template carriage 44 slidably received in the slot 38 of the housing 32. The template carriage includes opposed superior and inferior ends 46 and 48 respectively. The inferior end 48 of the template carriage 44 defines a male dovetail 50 dimensioned to be slidably received within the dovetailed slot 24 of any of the tibial templates 12 in the system. A threaded aperture 54 extends upwardly from the inferior surface 48 of the template carriage 44 centrally through the dovetail 50. A side portion of the template carriage 44 is characterized by a plurality of detents 56. Individual detents 56 are selectively alignable with the threaded aperture 40 extending through the side wall 36 of the housing 32. The particular detent 56 that aligns with the threaded aperture 40 depends upon the relative sliding position of the template carriage 44 in the slot 38 of the housing 32. As illustrated in FIG. 16 the plurality of detents 56 are aligned along an axis which is at an acute angle to the vertical, and preferably at an angle in the range of 5° to 10°. Thus detents 56 closer to the inferior end 48 will be further from the side wall 36 of the femoral resection guide spacer 30.

The femoral resection guide spacer 30 further includes a lateral knob 58 having a threaded portion threadedly engaged in the threaded aperture 40 of the side wall 36. An end of the lateral knob 58 is selectively engageable with a detent 56 in the template carriage 44. Thus, loosening of the lateral knob 58 enables the template carriage 44 to be slid upwardly or downwardly within the slot 38 of the housing 32. By virtue of the angular disposition of the detents 56, when the lateral locking knob 58 is loosened, the template carriage automatically drops to the point where the next higher detent 56 contacts the end of the lateral knob 58. Tightening of the lateral knob 58 securely locks the template carriage 44 in a selected position relative to the housing 32. As shown in FIG. 15, the template carriage 44 is provided with an indicator line 59 that is selectively alignable with the indicia 42 on the housing 30. The particular alignment of the indicator line 59 with the indicia 42 indicates the relative detent 56 with which the lateral knob 58 is threadedly engaged. This information is useful in the selection of a bearing for the prosthetic component as explained further below.

The femoral resection guide spacer 30 further includes an inferior knob 60 which passes through the notch 26 in the handle 22 of the tibial template 12 and which further threadedly engages in the threaded aperture 54 in the template carriage 44. Loosening of the inferior knob 60 enables the dovetail slot 24 of a selected tibial template 12 to be slidably mounted on the male dovetail 50 of the template carriage 44. Tightening of the inferior knob 60 securely locks the selected tibial template 12 to the template carriage 44.

The femoral resection guide spacer 30 further includes a projection 61 as shown in FIG. 14. The projection 61 extends rigidly from the housing 32 and substantially parallel to the inferior surface 20 of a tibial template 12 mounted on the femoral resection guide spacer 30. It will be appreciated that the distance "T" between the superior surface of the projection 61 and the inferior surface 20 of the tibial template 12 defines the prosthetic gap and will depend upon the thickness "t" of the handle 22 of the particular tibial template 12 selected.

Figure 17:
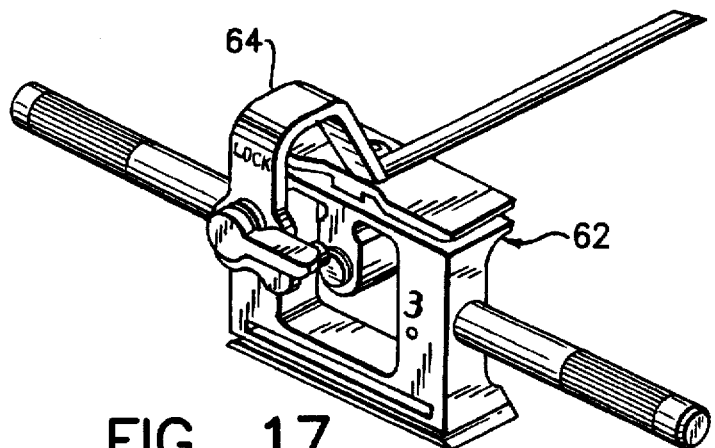
FIG. 17 is a perspective view of a femoral resection guide to which is secured a femoral guide yoke
Figure 18:
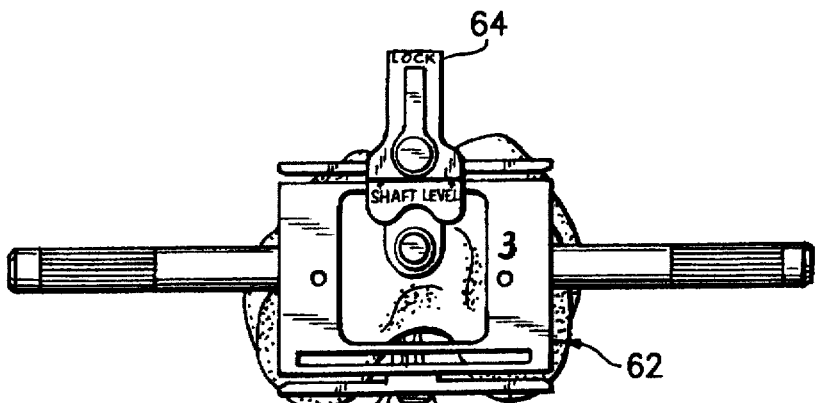
FIG. 18 is a front elevational view of the femoral resection guide and yoke of FIG. 17.
Figure 19:
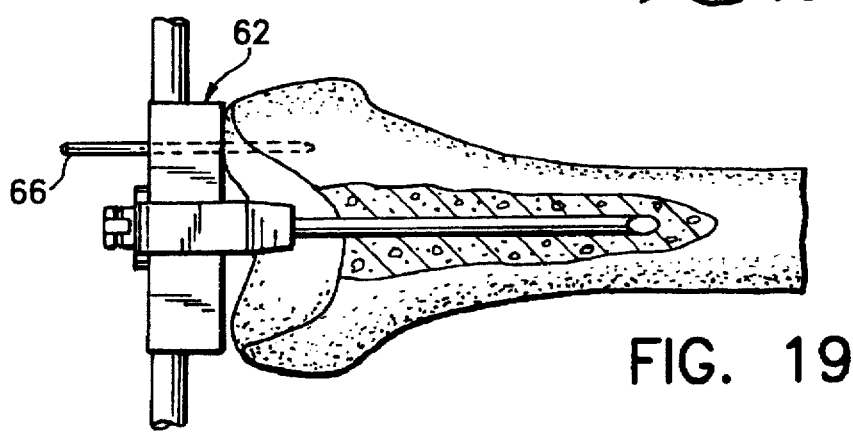
FIG. 19 is a top plan view of the femoral resection guide and yoke.

Referring to FIGS. 17–19, the system of the subject invention further includes a plurality of differently sized femoral resection guides 62 corresponding respectively to the sizes of the selected templates. The femoral resection guide 62 corresponding to the selected femoral and tibial templates 10 and 12 is mounted to a femoral guide yoke 64 as shown in FIG. 17. The yoke 64 is used to center the femoral resection guide 62 between the femoral epicondyles as shown in FIG. 18. The femoral resection guide 62 is the same width as the corresponding femoral component. Thus, the surgeon checks to ensure that the femoral resection guide 62 does not overhang the femoral articulate surface excessively. The femoral resection guide 62 is then partially stabilized using a pin 66 as shown in FIG. 19. A hole is then drilled up the femur. This establishes the flexion orientation of the femoral component.

Figure 20:
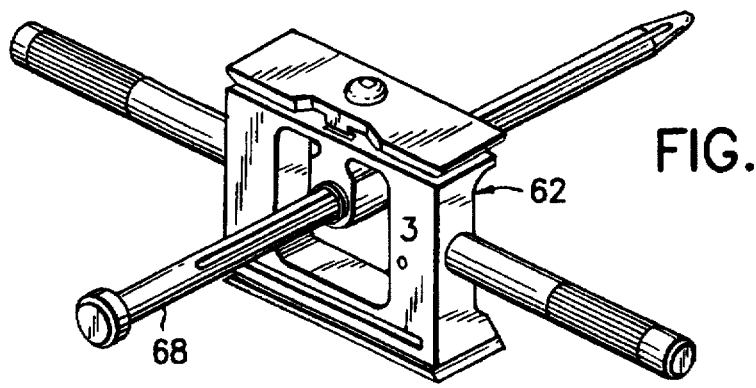
FIG. 20 is a perspective view of the femoral resection guide and I/M rod.

As shown in FIG. 20, the yoke 64 may be removed from the femoral resection guide 62, and an I/M rod 68 is inserted into the femoral resection guide 62. The rod 68 is then inserted into the previously drilled femoral shaft hole in the femur.

Figure 21:
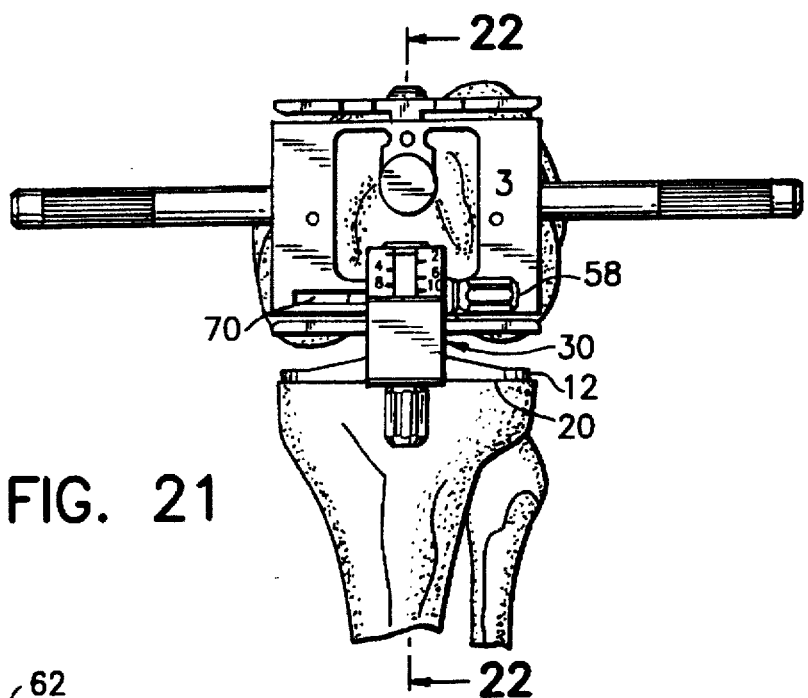
FIG. 21 is a front elevational view of the femoral resection guide mounted to the femoral resection guide spacer.
Figure 22:
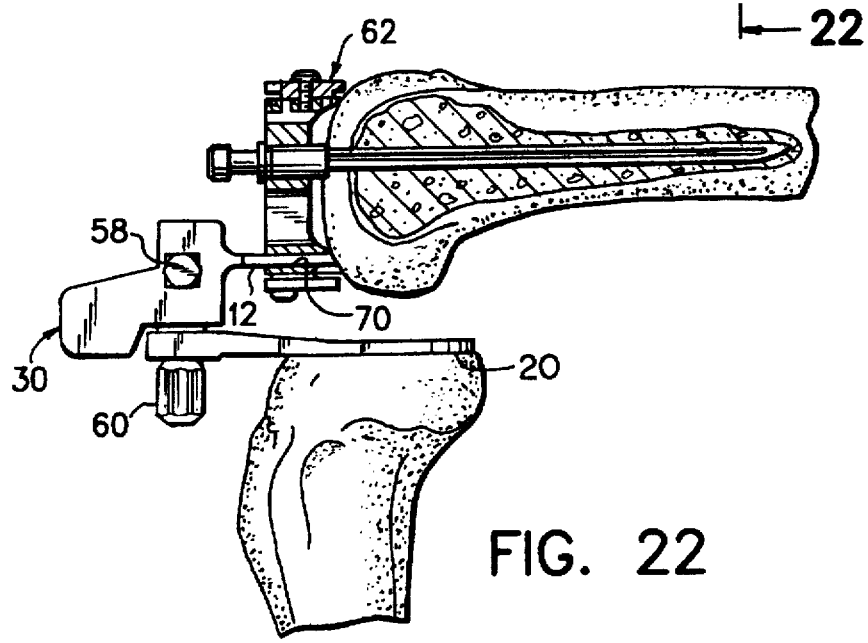
FIG. 22 is a cross-sectional view taken along line 22—22 in FIG. 21.

Referring to FIGS. 21 and 22, the projection 61 of the femoral resection guide spacer 30 may then be inserted into the slot 70 of the femoral resection guide 62 or adjacent the inferior surface of the femoral resection guide spacer 30 such that the inferior surface 20 of the tibial template 12 rests on the resected surface of the tibia. The function of the femoral resection guide spacer 30 and the tibial template 12 is to reproduce the flexion gap and to balance medial and lateral ligamentous tension. This will axially position the A-P femoral resection guide 62 so as to produced balanced flexion tension and proper axial plane alignment. If the femoral resection guide spacer 30 is too tight, the tibial resection is too high. As a result, further resection of the tibia may be required. If the joint is loose in flexion, the template carriage 44 is moved to a "thicker position" by loosening the lateral knob 58 just enough to allow the template carriage 44 to drop to the next position of the detents 56 as indicated by the relative alignments of the indicator line 59 and the indicia 42. Further slow loosening of the lateral knob 58 will allow the template carriage 44 to drop to the next detent 56 to yet thicker positions. It will be appreciated that each such movement of the template carriage 44 will generate a corresponding movement of the tibial template 12 connected thereto. The thickness that provides the best approximation of normal flexion tension of the ligaments is selected and the lateral knob 58 is tightened in that thickness position. This final position of the template carriage 44 will most likely correspond to the thickness of the bearing that will be used between the tibial and femoral components of the prosthesis. Once the proper ligamentous tension is achieved, a second pin is placed in the femoral resection guide 62 to further stabilize the guide. The femoral resection is then carried out using the femoral resection guide 62. The tibial template used in this procedure had been selected because it matched the size and shape of the resected tibia. Thus the tibial template will engage the hard cortical bone and will not damage the softer inner bone as had occurred when a small spacer block or thickness adapter was used in the prior art.

Figure 23:
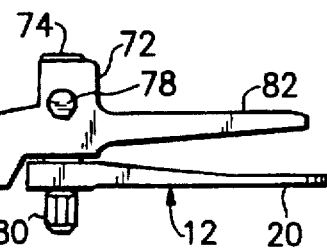
FIG. 23 is a side elevational view of the tibial template and spacer block of the subject invention.

The tibial template 12 is then removed from the femoral resection guide spacer 30 and is assembled onto the resection checking spacer 71, as illustrated in FIG. 23. More particularly, the resection checking spacer 71 includes a housing 72 into which a template carriage 74 is slidably received. The construction of the housing 72 and the template carriage 74 are identical to the construction of the housing 32 and the template carriage 44 on the femoral resection guide spacer 30 described above. In particular, a lateral knob 78 is threadedly engaged in the housing 72 for locking the template carriage 74 in a fixed elevational position relative to the housing 72. Indicia on the housing 72 and the template carriage 74 identifies the relative elevational position. The lateral knob 78 is initially loosened to enable the indicia on the housing 72 and template carriage 74 to be aligned in the position last used on the resection guide spacer 30.

The housing 72 further includes an inferior knob 80 functionally similar to the inferior knob 60 on the femoral resection guide spacer 30 described above. The inferior knob 80 functions to lock the tibial template 12 onto a male dovetail substantially identical to the male dovetail 50 on the inferior end of the template carriage 44 described above. The housing 72 of the resection checking spacer 71 further includes a projection 82 projecting therefrom and generally parallel to the tibial template 12. As explained in detail above, the handles 22 of the tibial templates 12 define different respective thicknesses that vary in accordance with the plan view size of the engaging portion of the tibial template 12. Thus, as with the femoral resection guide spacer 30, the distance between the superior surface of the projection 82 and the inferior surface 20 of the selected template 12 will vary in accordance with the thickness of the selected tibial template 12 so that the prosthetic gap will be larger for larger prosthetic components.

Figure 24:
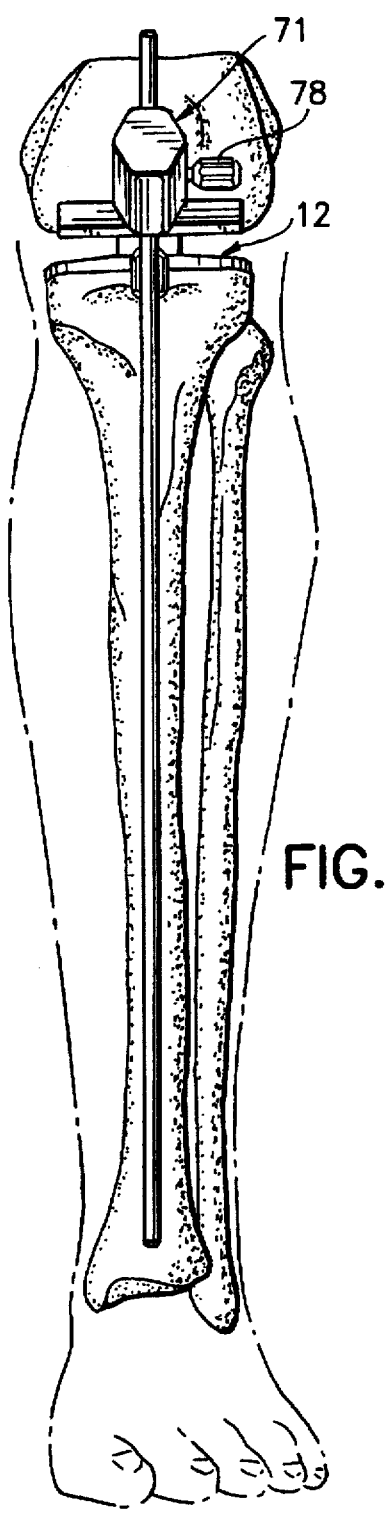
FIG. 24 is a front elevational view of a tibial template and resection checking spacer being used to check flexion tension.

The surgeon uses the assembled resection checking spacer 71 and tibial template 12 to first check flexion tension and alignment as shown in FIG. 24. The tibial resection may be adjusted if necessary based on this check. If necessary, the setting of the template carriage 74 of the spacer block 71 may be adjusted by loosening the lateral knob 78 and permitting the template carriage 74 to automatically incrementally drop. The final setting of the template carriage 74 also is used to establish ligamentous tension in extension.

Figure 25:
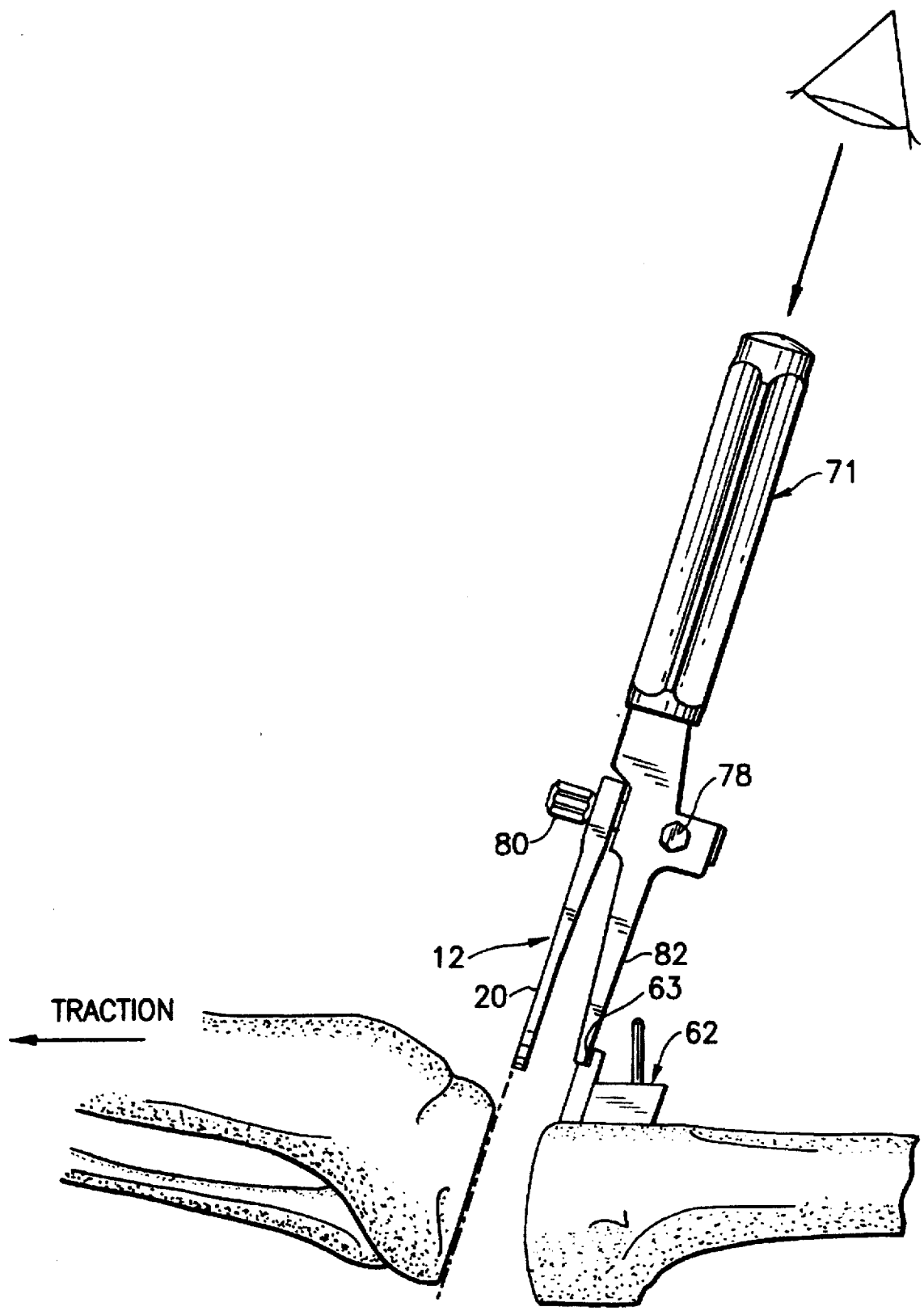
FIG. 25 is a side elevational view of the tibial template and resection checking spacer used to check alignment of the tibial resection.

Extension tension is checked as shown in FIG. 25. In particular, the assembled resection checking spacer 71 and tibial template 12 are placed in the notch 63 in the distal femoral resection guide, holding the projection 82 of the spacer block 71 flat against the surfaces of the notch 63 in the femoral resection guide 62. The tibia is then fully extending and traction is applied to simulate normal ligamentous tension as shown in FIG. 25. The surgeon then sights along the shaft of the resection checking spacer 71 to determine if the inferior surface 20 of the tibial template 12 is aligned with the tibial resection. If the tibial template 10 is misaligned by more than 1 mm, the distal femoral resection guide is moved so that the fixation pins 66 are in a new set of holes that will produce a proper extension gap.

Figure 26:
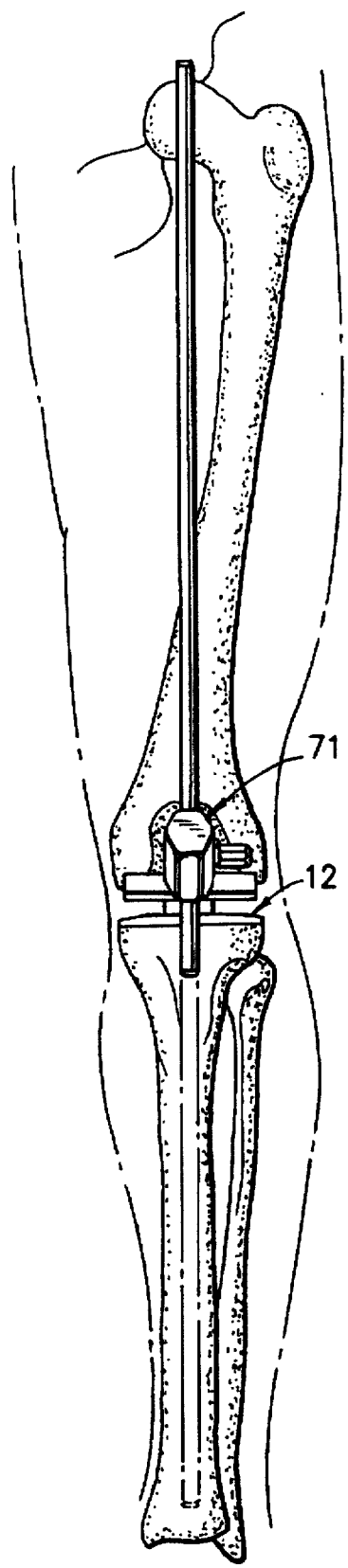
FIG. 26 is a front elevational view of the tibial template and resection checking spacer used to check extension tension.
Figure 27:
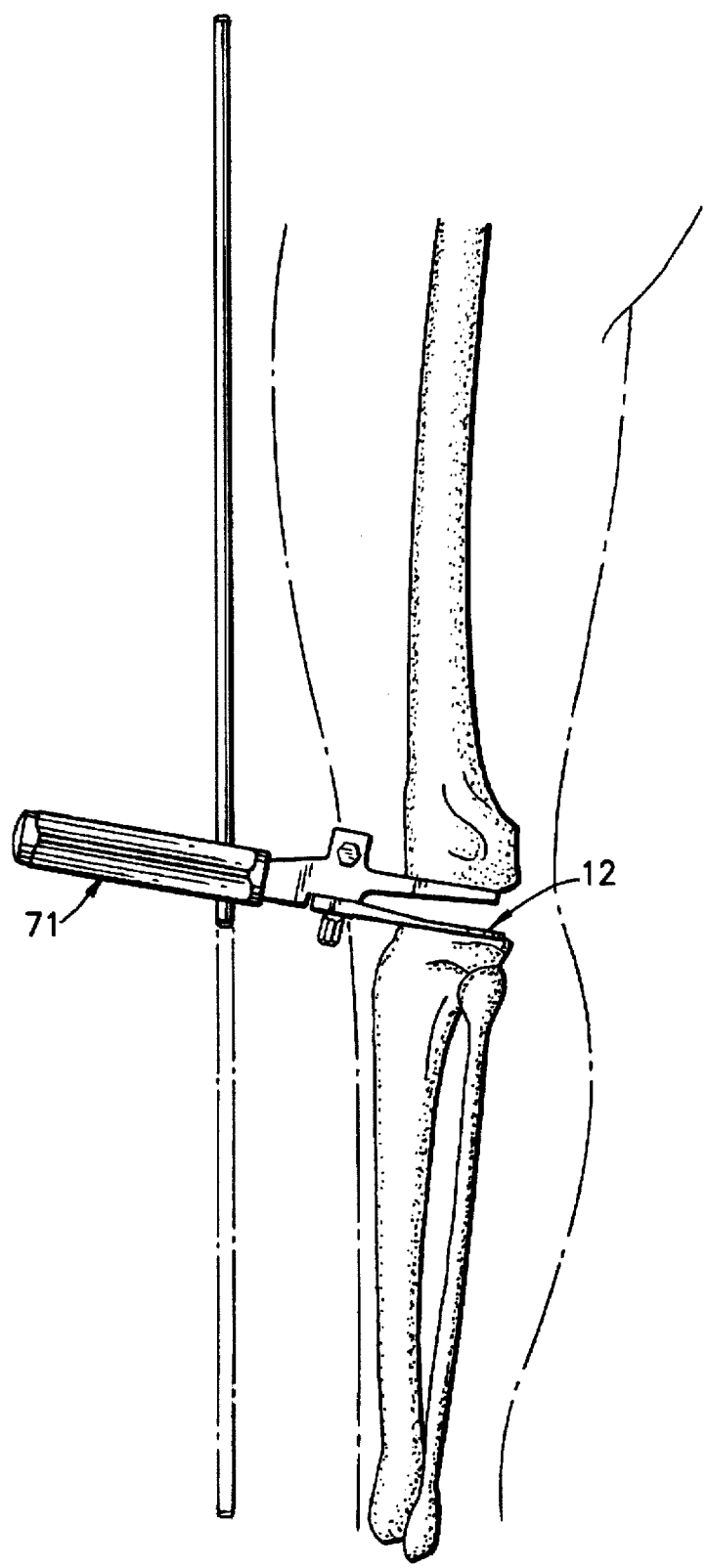
FIG. 27 is a side elevational view of the assembly shown in FIG. 26.

The extension tension and limb alignment are then checked using the assembled tibial template 12 and resection checking spacer 71 as shown in FIG. 26 and 27 to establish the distal femoral resection level and to re-approximate the extension prosthetic gap. In making any subsequent resection adjustments, the surgeon must ensure that the extension gap is equal to the flexion gap. Thereafter, the surgeon proceeds with the femoral finishing resections, the final tibial preparation, trial reduction, patellar preparation, and the final component implantation. The steps using spacer block 71 and tibial template 12 ensure that forces on the resected tibia are exerted by a template 12 conforming to the size and shape of the resected tibia. Thus compression or other damage to soft bone tissue are avoided.

While the invention has been described with respect to a preferred embodiment, it is apparent that various changes can be made without departing from the scope of the invention. For example the system of the subject invention may be used for implantation of other prosthetic joints. Furthermore the object of matching the spacer footprint to the shape of the resected bone can be achieved with or without increasing the prosthetic gap for larger prosthetic components.

What is claimed is:

1. A template system comprising a plurality of templates for use with a corresponding plurality of prosthetic components of different respective sizes, said templates in said template system defining different respective thicknesses for establishing differently dimensioned prosthetic gaps associated with each said corresponding prosthetic component, each said template further defining a plan view surface area, templates in said system that have greater thicknesses further defining larger plan view surface areas.

2. A template system as in claim 1, further comprising a spacer, said spacer being engageable with any one of said templates for establishing the prosthetic gap.

3. A template system as in claim 2, wherein said spacer includes an adjustable template carriage having a portion for engaging any of said templates of different respective thicknesses.

4. A template system comprising a plurality of templates for use with a corresponding plurality of prosthetic components of different respective sizes, said templates in said template system defining different respective thicknesses for establishing differently dimensioned prosthetic gaps associated with each said corresponding prosthetic component, said system further comprising a spacer, said spacer being engageable with any one of said templates for establishing the prosthetic gap, said spacer including an adjustable template carriage having a portion for engaging any of said templates of different respective thicknesses, said spacer including a housing in which said adjustable template carriage is slidably moveable, and further including locking means for fixing the template carriage relative to said housing.

5. A template system as in claim 4, wherein said template carriage includes a plurality of detents disposed at an acute angle to the vertical, and wherein said housing includes a locking knob engageable with said detents such that, with the spacer in the vertical position, loosening of the locking knob causes the template carriage to drop to the next detent for automatic adjustment of the spacer.

6. A prosthetic joint system for surgical implantation of a prosthetic joint in a patient, said system comprising a plurality of different dimensioned prosthetic joints for implantation respectively in patients of different sizes, each of said prosthetic joints comprising a first prosthetic component for mounting to a first bone of said joint, a second prosthetic component for mounting to a second bone of said joint and a bearing for engagement between said first and second prosthetic components, said system further comprising a corresponding plurality of templates having different respective plan view configurations corresponding to a plurality of different configurations of said first bone of said joint, said templates being of different respective thicknesses which increase as the plan view surface area of the respective template increases, such that said templates enable larger prosthetic gaps for larger prosthetic components.

7. The system of claim 6, wherein each said template is provided with unique indicia corresponding to a respective size of an associated prosthetic component.

8. The system of claim 6, further comprising a spacer releasably securable with any selected one of said templates for establishing said prosthetic gap.

9. A prosthetic joint system for surgical implantation of a prosthetic joint in a patient, said system comprising a plurality of different dimensioned prosthetic joints for implantation respectively in patients of different sizes, each of said prosthetic joints comprising a first prosthetic component for mounting to a first bone of said joint, a second prosthetic component for mounting to a second bone of said joint and a bearing for engagement between said first and second prosthetic components, said system further comprising a corresponding plurality of templates having different respective plan view configurations corresponding to a plurality of different configurations of said first bone of said joint, said templates being of different respective thicknesses which increase as the plan view surface area of the respective template increases, such that said templates enable larger prosthetic gaps for larger prosthetic components, said system further comprising a spacer releasably securable with any one of said templates for establishing said prosthetic gap, said spacer including a housing and a template carriage adjustably movable to said housing, said template carriage including portions of said spacer that are releasably securable with any of said templates.

10. The system of claim 9, wherein said template carriage is adjustably movable in a selected direction relative to said housing and includes a plurality of detents disposed at an acute angle to said direction, and wherein said housing includes a locking knob engageable with said detents such that loosening of the locking knob causes ,the template carriage to drop to an adjacent one of said detents for automatic adjustment of the template carriage.

11. A prosthetic joint system for surgical implantation of a prosthetic joint in a patient, said system comprising a plurality of different dimensioned prosthetic joints for implantation respectively in patients of different sizes, each of said prosthetic joints comprising a first prosthetic component for mounting to a first bone of said joint, a second prosthetic component for mounting to a second bone of said joint and a bearing for engagement between said first and second prosthetic components, said system further comprising a corresponding plurality of templates having different respective plan view configurations corresponding to a plurality of different configurations of said first bone of said joint, said templates being of different respective thicknesses which increase as the plan view surface area of the respective template increases, such that said templates enable larger prosthetic gaps for larger prosthetic components, each of said templates including a gauging end and a handle, the gauging ends of said templates having different plan view surface areas for gauging dimensions of the first bone, the handles of said templates defining thicknesses which vary with the area of the respective gauging portions.

12. The system of claim 11, further comprising a first and second spacer having means for selective releasable engagement with the handle of any one of said templates, said first spacer defining a resection guide positioner for establishing desired locations for resecting the second bone of the joint to achieve a desired prosthetic gap, said second spacer being usable after resection of said second bone for establishing the prosthetic gap and for selecting an appropriate thickness for said bearing.

13. The system of claim 12, wherein each of said spacers includes a housing and template carriage adjustably mounted in said housing, said template carriage defining portions of each said spacer that are selectively and releasably engageable with any of said templates, whereby adjustment of said template carriage in said housing of either of said spacers enables selection of a bearing with a thickness for achieving optimum ligamentous tension.

14. A spacer and template system for determining prosthetic joint size and for establishing a prosthetic gap during surgery for implantation of a prosthetic joint between first and second bones, said system comprising a plurality of templates having different respective plan view sizes and shapes conforming to a range of possible sizes and shapes for said first bone and further conforming to different available dimensions of said prosthetic joints, wherein said templates are of different respective thicknesses, with said thicknesses increasing as the plan view surface area of the respective templates increase; and a spacer releasably connectable to any selected one of said templates for establishing a prosthetic gap between said first and second bones, said spacer and said selected template releasably connected thereto being disposed such that said template abuts said first bone and substantially conforms to said size and shape of said first bone for preventing intraoperative damage to inner portions of said bone.

15. A spacer and template system for implantation of a prosthetic joint between first and second bones, said system comprising a plurality of templates having different respective plan view sizes and shapes conforming to a range of possible sizes and shapes for said first bone and further conforming to different available dimensions of said prosthetic joints, wherein said templates are of different respective thicknesses, with said thicknesses increasing as the plan view surface area of the respective templates increase; and a spacer releasably connectable to any selected one of said templates for establishing a prosthetic gap between said first and second bones, said spacer and said selected template releasably connected thereto being disposed such that said template abuts said first bone and substantially conforms to said size and shape of said first bone for preventing intraoperative damage to inner portions of said bone, said spacer including a housing and a template carriage adjustably mounted in said housing, any of said templates being selectively releasably engageable with said template carriage of said spacer.

* * * * *